(12) United States Patent
Connell et al.

(10) Patent No.: US 7,198,611 B2
(45) Date of Patent: Apr. 3, 2007

(54) DIALYSIS CONNECTOR AND CAP HAVING AN INTEGRAL DISINFECTANT

(75) Inventors: Brian Connell, Evanston, IL (US); Bill Griswold, Bristol, WI (US); Raf Castellanos, Roselle, IL (US); Tom Johnson, Gurnee, IL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 949 days.

(21) Appl. No.: 10/074,532

(22) Filed: Feb. 11, 2002

(65) Prior Publication Data

US 2003/0153865 A1 Aug. 14, 2003

(51) Int. Cl.
*A61M 1/00* (2006.01)
(52) U.S. Cl. ...................................... 604/30
(58) Field of Classification Search ............... 604/905, 604/415, 284, 256, 244, 206, 167.01–167.06, 604/165.01–165.04, 91, 88, 86, 83; 285/331, 285/386
See application file for complete search history.

(56) References Cited

U.S. PATENT DOCUMENTS

| | | | |
|---|---|---|---|
| 3,447,161 A | 6/1969 | Weikel | |
| 3,858,580 A | 1/1975 | Ogle | |
| 3,986,508 A * | 10/1976 | Barrington | 604/411 |
| 4,201,208 A | 5/1980 | Cambio, Jr. | |
| 4,239,041 A * | 12/1980 | Popovich et al. | 604/28 |
| 4,334,551 A | 6/1982 | Pfister | |
| 4,354,490 A * | 10/1982 | Rogers | 604/403 |
| 4,432,764 A | 2/1984 | Lopez | |
| 4,432,766 A | 2/1984 | Bellotti et al. | |
| 4,440,207 A * | 4/1984 | Genatempo et al. | 150/154 |
| 4,457,749 A * | 7/1984 | Bellotti et al. | 604/29 |
| 4,511,359 A | 4/1985 | Vaillancourt | |
| 4,526,572 A | 7/1985 | Donnan et al. | |
| 4,551,146 A | 11/1985 | Rogers | |

(Continued)

FOREIGN PATENT DOCUMENTS

CA 1256343 6/1989

(Continued)

OTHER PUBLICATIONS

International Search Report for International Patent Application No. PCT/US2005/038424 that corresponds to the present application and of which the references cited above as cited therein.

*Primary Examiner*—Manuel Mendez
(74) *Attorney, Agent, or Firm*—Joseph P. Reagen; Bell, Boyd & Lloyd LLC (57) ABSTRACT

Apparatuses and methods for providing sterile connection during, for example, dialysis therapy. The present invention provides a connector and a cap therefore that easily and readily attaches to a dialysate container and a catheter inserted into a patient's peritoneal cavity. The connector and the cap enable the dialysate to readily transport between the container and the peritoneal cavity while minimizing the potential of contamination therein due to, for example, handling during use. The connector includes a shell that encloses a cap. The cap houses a slit septum and also includes a sealed disinfectant within an interior receptacle. When the catheter or catheter set attaches to the cap, the seal breaks and the disinfectant spreads over the threads between the catheter set and the cap.

6 Claims, 3 Drawing Sheets

U.S. PATENT DOCUMENTS

| | | |
|---|---|---|
| 4,580,816 A | 4/1986 | Campbell et al. |
| 4,610,469 A * | 9/1986 | Wolff-Mooij ............... 285/260 |
| 4,617,012 A | 10/1986 | Vaillancourt |
| 4,623,327 A | 11/1986 | Mahurkar |
| 4,624,664 A | 11/1986 | Peluso et al. |
| 4,655,762 A | 4/1987 | Rogers |
| 4,675,004 A | 6/1987 | Hadford et al. |
| 4,701,159 A | 10/1987 | Brown et al. |
| 4,770,652 A | 9/1988 | Mahurkar |
| 4,810,241 A | 3/1989 | Rogers |
| 4,816,221 A | 3/1989 | Harvey et al. |
| 4,842,582 A | 6/1989 | Mahurkar |
| 4,895,570 A | 1/1990 | Larkin |
| 4,941,517 A | 7/1990 | Galloway |
| 5,009,636 A | 4/1991 | Wortley et al. |
| 5,100,394 A | 3/1992 | Dudar et al. |
| 5,137,524 A | 8/1992 | Lynn et al. |
| 5,188,593 A | 2/1993 | Martin |
| 5,190,534 A | 3/1993 | Kendell |
| 5,211,638 A | 5/1993 | Dudar et al. |
| 5,242,425 A | 9/1993 | White et al. |
| 5,263,930 A | 11/1993 | Ensminger |
| 5,269,764 A | 12/1993 | Vetter et al. |
| 5,279,605 A | 1/1994 | Karrasch et al. |
| 5,378,230 A | 1/1995 | Mahurkar |
| 5,393,101 A | 2/1995 | Matkovich et al. |
| 5,437,650 A | 8/1995 | Larkin et al. |
| 5,456,675 A | 10/1995 | Wolbring et al. |
| 5,489,278 A | 2/1996 | Abrahamson |
| 5,501,676 A | 3/1996 | Niedospial et al. |
| 5,507,733 A | 4/1996 | Larkin et al. |
| 5,571,093 A | 11/1996 | Cruz et al. |
| 5,620,427 A | 4/1997 | Werschmidt et al. |
| 5,694,978 A | 12/1997 | Heilmann et al. |
| 5,743,892 A | 4/1998 | Loh et al. |
| 5,776,116 A | 7/1998 | Lopez et al. |
| 5,782,808 A | 7/1998 | Folden |
| 5,810,398 A | 9/1998 | Matkovich |
| 6,027,489 A | 2/2000 | Galato |
| 6,079,432 A | 6/2000 | Paradis |
| 6,183,465 B1 | 2/2001 | Meier et al. |
| 6,911,025 B2 | 6/2005 | Miyahara |
| 2002/0010437 A1 | 1/2002 | Lopez et al. |
| 2003/0006610 A1 | 1/2003 | Werth |
| 2003/0144647 A1 | 7/2003 | Miyahara |
| 2003/0184090 A1 | 10/2003 | Guala |
| 2004/0087986 A1 | 5/2004 | Ott |
| 2004/0238776 A1 | 12/2004 | Peters et al. |

FOREIGN PATENT DOCUMENTS

| | | |
|---|---|---|
| DE | 2853635 | 6/1980 |
| EP | 0 092 528 | 10/1983 |
| EP | 0 554 722 | 8/1993 |
| EP | 1243280 | 9/2002 |
| EP | 1331020 | 7/2003 |
| GB | 2 067 075 | 7/1981 |
| GB | 2343723 | 5/2000 |
| JP | 09192216 A | 7/1997 |
| JP | 10248924 A | 9/1998 |
| JP | 11057419 A | 3/1999 |
| JP | 11-128359 | 5/1999 |
| JP | 2000014772 A | 1/2000 |
| JP | 2000140099 A | 5/2000 |
| WO | WO 83/00812 | 3/1983 |
| WO | WO94/23775 | 10/1994 |
| WO | WO 95/15194 | 6/1995 |
| WO | WO 97/00095 | 1/1997 |
| WO | WO 97/35634 | 10/1997 |
| WO | WO01/85249 A | 11/2001 |
| WO | WO2004/033023 | 4/2004 |
| WO | WO2004/071557 | 8/2004 |

* cited by examiner

DIALYSIS CONNECTOR AND CAP HAVING AN INTEGRAL DISINFECTANT

BACKGROUND OF THE INVENTION

The present invention relates generally to medical treatments. More specifically, the present invention relates to medical connectors for use in medical treatments, such as Peritoneal Dialysis ("PD").

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

PD uses a dialysis solution or dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs by diffusion and osmosis because there is an osmotic gradient across the peritoneal membrane. The spent dialysate is drained from the patient's peritoneal cavity to remove the waste, toxins and water from the patient. New dialysate replaces the spent dialysate and the process repeats.

During dialysis therapy, a dialysis fluid exchange generally includes draining spent dialysis fluid from the peritoneal cavity and filling the peritoneal cavity with fresh dialysate. Keeping track of the amounts or volumes of dialysis solution drained from and supplied to the peritoneal cavity is important for proper dialysis therapy: A typical amount of dialysate solution drained from and supplied to the peritoneal cavity of an adult during an exchange can be roughly two to three liters. Dialysis fluid exchanges have been performed manually, usually by the patient, or automatically, by an automated dialysis machine.

In the manual PD technique, known as Continuous Ambulatory Peritoneal Dialysis ("CAPD"), a catheter is implanted into the peritoneal cavity of the patient. A dialysis solution ("dialysate") is introduced through the catheter into the peritoneal cavity of a patient. Typically, a container of the dialysate connects to a connector, which in turn couples to the catheter. To start the flow of dialysate into the peritoneal cavity, a clamp on a tube connecting the container to the connector is loosened or a valve is opened. In many cases the container is located vertically above the patient and gravity fed into the peritoneal cavity.

In the Automated Peritoneal Dialysis technique ("APD"), dialysis machines use one or more fluid pumps to perform the dialysate exchanges. The pump pumps spent dialysate fluid out of the peritoneal cavity during the drain mode and pumps dialysate into the cavity during the fill mode.

In either PD technique, once the dialysate reaches the patient, dialysis of urea, toxic waste and the like takes place between the dialysate and the blood passing through blood vessels in the peritoneum, which is the lining of the peritoneal cavity. The dialysate remains in the peritoneal cavity for several hours. Thereafter, the dialysate is removed from the peritoneal cavity carrying with it diffused breakdown products from the blood. In CAPD, one method for removing the spent dialysate is to lower the dialysate container outside of the body and let the dialysate drain into the container.

The spent container is disconnected and discarded, wherein a new container of dialysate fluid is attached and the process is repeated. This process may be repeated several times or continuously repeated. Because many patients perform the PD (CAPD or APD) procedure themselves, it is important that the connector which connects the dialysate container to the catheter is easy to use and provides a secure connection.

A frequent problem that occurs with PD is peritoneal infection or peritonitis which can readily occur given the repeated disconnecting and reattaching of the dialysate containers. Peritonitis results if connections are made between the peritoneal catheter and the connector communicating with the dialysis container in a maimer that permits even a very small number of microorganisms to enter the catheter. The microorganisms will be flushed into the peritoneal cavity. Peritonitis can occur even when extreme caution is observed in making and unmaking the connections. Peritonitis can be painful and can temporarily diminish the hydraulic permeability of the peritoneal membrane, rendering the renal treatment less successful.

Methods to prevent peritonitis have included thoroughly cleansing the connector and the tube connecting the dialysate container before the connection is made. For instance, the connector can be immersed in povidone iodine, betadine or other type of disinfectant. These methods however are messy, time consuming, effort consuming, inconsistent and may be subject to overkill in order to achieve consistently effective results. Hospital workers, as another precaution, typically wear sterile rubber gloves to prevent or guard against any possible peritoneal invasion of bacteria. However, the spread of contamination can still occur due to, for example, a cut in the glove or other like condition.

Accordingly, the frequent connections that must be made and broken between the catheter residing in the peritoneal cavity and a succession of dialysate containers has created a need to ensure the sterilization of connectors used in performing CAPD and APD. Attempts have been made to saturate an absorbent material with disinfectant and dispose the material in the connector such that it contacts the tube/connector interface. A need still exists however to improve the efficiency, effectiveness and cost of providing sterile connections for PD.

A continuing need therefore exists to provide a simple and effective method and apparatus for performing PD, including CAPD and APD both in hospitals and at a patient's home.

SUMMARY OF THE INVENTION

The present invention relates to a connector and a cap that are easily and readily attachable to a dialysate container and a catheter inserted into a patient's peritoneal cavity. The connector and the cap enable the dialysate to be readily transported between the container and the peritoneal cavity while minimizing the potential of contamination therein due to, for example, handling during use.

To this end, in an embodiment of the present invention, a connector includes a shell that encloses a cap. The cap houses a slit septum. The cap also includes a sealed disinfectant within an interior receptacle. The seal in an embodiment is a crosslinked elastomeric seal, e.g., a silicone seal. In one embodiment, the disinfectant includes a povidone iodine or PVP-I. The connector is also initially packaged including a tip protector that encloses the shell/cap assembly and provides a barrier to microbial contamination prior to use.

In another embodiment of the present invention, a cap for use in a connector making a resealable fluid path is provided. The cap includes a body that defines a fluid flow passage and a disinfectant receptacle. The receptacle houses the disinfectant. A seal is disposed within the body. The seal seals the disinfectant between the seal and the receptacle.

In an embodiment, the body defines an opening that receives a fluid communication member. The fluid communication member is capable of displacing the seal when the body receives the member.

In an embodiment, the disinfectant disperses between an outer wall of the fluid communication member and an inner wall of the body when the seal is displaced.

In an embodiment, the body defines outer threads.

In an embodiment, the outer threads engage mating threads of a shell and enable the shell to translate with respect to the body. The translating shell causes a sealed end of the body to be pierced.

In an embodiment, the body defines inner threads.

In an embodiment, the inner threads engage mating threads of a fluid communication member and enable the member to translate with respect to the body.

The translating member causes the seal to be displaced.

In an embodiment, the seal is moveable.

In an embodiment, the body includes a tube portion that defines the fluid flow passage. The disinfectant receptacle resides about the tube portion.

In an embodiment, a portion of the passage is sized to house a member that deforms to seal about a tube.

In an embodiment, the member automatically closes when the tube is removed from the member.

In still another embodiment of the present invention, a connector for making a resealable fluid path is provided. The connector includes a cap that defines a fluid flow passage. The cap seals an amount of disinfectant, such as a continuous quantity thereof. A shell moveably engages the cap. The shell includes a fluid communication member. The fluid communication member is capable of piercing a sealed end of the cap and fluidly communicating with the fluid flow passage when the shell moves with respect to the cap.

In an embodiment, the disinfectant includes povidone iodine.

In an embodiment, the connector includes a tip protector that engages the shell.

In an embodiment, the shell attaches to a fluid line running to a dialysate container and the cap attaches to a fluid line running to a patient.

In an embodiment, the sealed end of the cap includes a slit septum.

In an embodiment, the connector includes an elastomeric seal that seals the disinfectant about the fluid flow passage.

In still another embodiment of the present invention, a method for providing a sterile connection of a dialysate line is provided. The method includes providing a cap that has a passage and maintains a seal that houses a disinfectant. A first member connects to a first end of the cap. The first member then fluidly communicates with a first dialysate line. A second member connects to a second end of the cap so as to displace the seal and the disinfectant. The second member then fluidly communicates with a second dialysate line.

In an embodiment, connecting the first member includes moving the first member so as to pierce a sealed end of the cap, which places the first member in fluid communication with the second member.

In an embodiment, the sealed end of the cap seals about the first member when the first member pierces the sealed end.

In an embodiment, the sealed end of the cap reseals when the first member is removed from the cap.

In an embodiment, rupturing the seal includes threading the second member into the cap and exerting pressure on the seal.

In an embodiment, connecting the second member includes displacing the disinfectant between the cap and the second member.

In an embodiment, the method further includes maintaining the disinfectant between the cap and the second member after the seal is displaced.

In an embodiment, the method includes removing the first member from the cap such that the sterile connection between the cap and the second member is maintained In an embodiment, the method includes removing a tip protector and connecting the second member in place of the tip protector.

In still another embodiment of the present invention, a method for providing PD is provided. The method includes the steps of providing a first member in fluid communication with a dialysate container, a second member in fluid communication with a peritoneal cavity of a patient, and a cap that has a sealed first end, a second end, a passage and maintains a seal that houses a disinfectant; connecting the first member to the sealed first end of the cap; connecting the second member to the second end of the cap so as to displace the seal and the disinfectant thereby causing the first member to pierce the sealed first end of the cap; filling the peritoneal cavity with an amount of fresh dialysate fluid; and removing the first member to automatically reseal the first end of the cap.

In an embodiment, the method includes removing an amount of spent dialysate fluid from the peritoneal cavity prior to filling the peritoneal cavity with the fresh dialysate fluid.

In an embodiment, the method includes connecting another first member to the first end, removing spent dialysate fluid from the peritoneal cavity and refilling the peritoneal cavity with fresh dialysate fluid.

In different embodiments, the filling and removing steps are performed manually or automatically.

It is therefore an advantage of the present invention to provide a dialysis connector that eliminates the need for the use and therefore handling of an additional cap to seal a catheter subsequent to use.

Moreover, an advantage of the present invention is to provide a dialysis connector that reduces the likelihood of peritonitis.

Another advantage of the present invention is to provide a dialysis cap that remains attached to a catheter set after use.

Still another advantage of the present invention is to provide a connector and a cap therefore having a septum that automatically reseals upon removal of the cap from a shell that couples to the dialysate container.

A further advantage of the present invention is to provide a dialysis connector employing a sealed disinfectant in conjunction with a releasable and resealable cap, which effectively minimizes the spread of microbial contamination to a catheter transfer set, and thus to the patient, during dialysis therapy.

Yet another advantage of the present invention is to provide a cap for use in PD, including CAPD and APD that contains a disinfectant and that cannot spill the disinfectant when a tip protector is removed.

Yet a further advantage of the present invention is to provide a cap for use in CAPD and APD that contains a continuous amount of a disinfectant and does not require an absorbent material to hold the disinfectant.

Still further, an advantage of the present invention is to provide a resealable cap enclosed within a protective shell prior to insertion of a catheter set.

Additionally, it is an advantage of the present invention to provide a resealable cap having a sealed disinfectant that displaces across threads of the cap and the transfer set.

Additional features and advantages of the present invention are described in, and will be apparent from, the following Detailed Description of the Invention and the Figures.

DETAILED DESCRIPTION OF THE INVENTION

The present invention provides a connector and a cap therefore that includes a disinfectant for any system requiring a connection, such as a connection of a first length of tubing or other conduit to a second length of tubing or other conduit, such as for PD. The present invention provides a safe and easy connection and method for introducing a disinfectant for a user/patient. The connector and cap therefore do not create a mess and do not make the user/patient perform special handling in order not to spill the disinfectant contained therein.

The method and apparatus for the present invention can be used to perform Continuous Ambulatory Peritoneal Dialysis ("CAPD") and Automated Peritoneal Dialysis ("APD"), collectively referred to herein as Peritoneal Dialysis ("PD"). It should be appreciated, however, that the connector and cap and method for using same can be used in a variety of other applications, particularly applications that insert a medical fluid into the body of a patient.

Figure 1A:
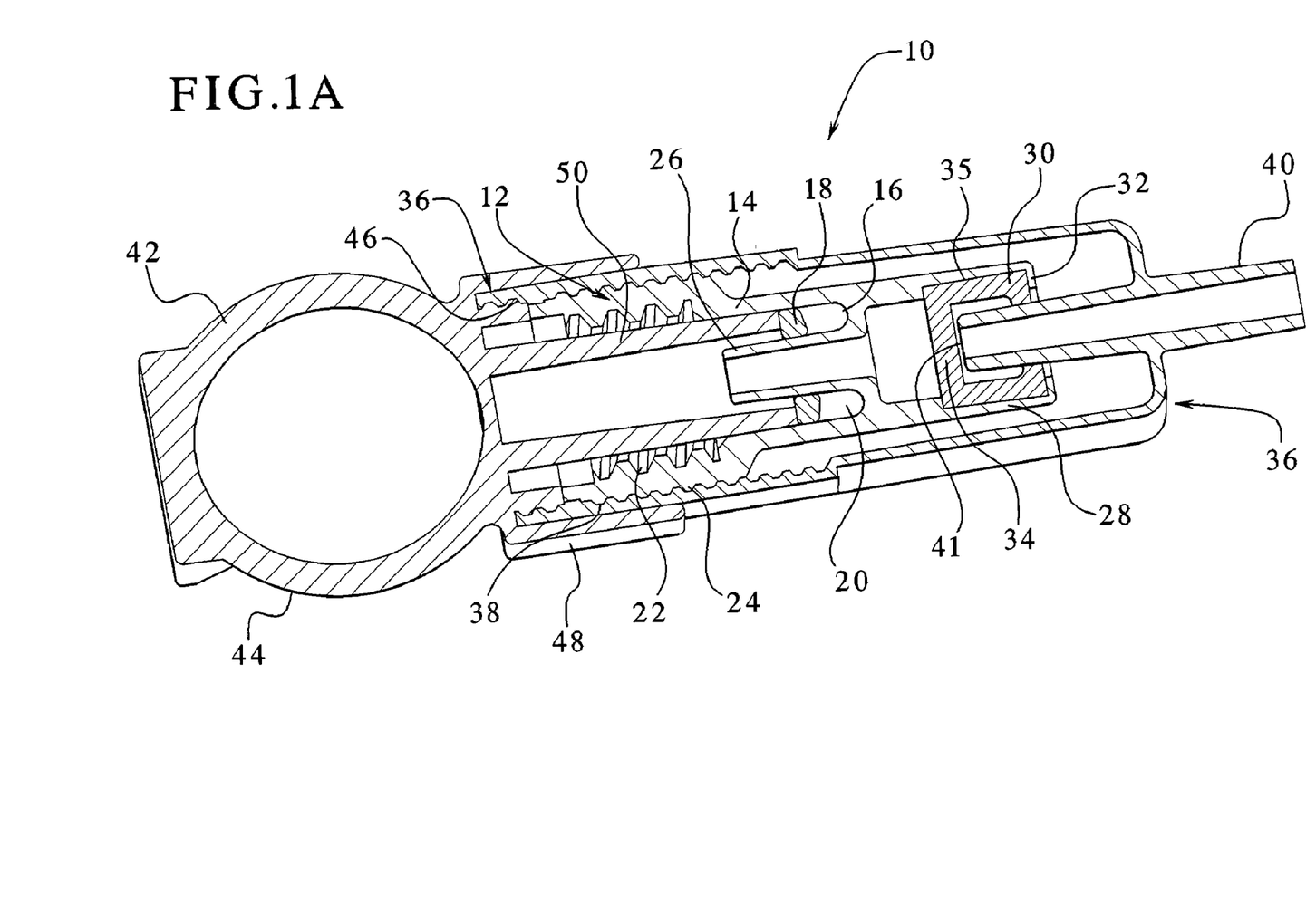
FIG. 1A is a perspective view of one embodiment of the dialysis connector and cap therefore of the present invention.
Figure 1B:
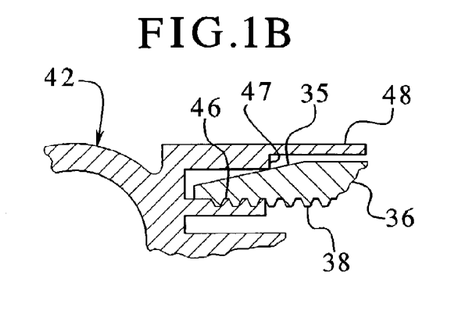
FIG. 1B is a schematic sectional view showing an embodiment of an interface between the shell and the tip protector.
Figure 1C:
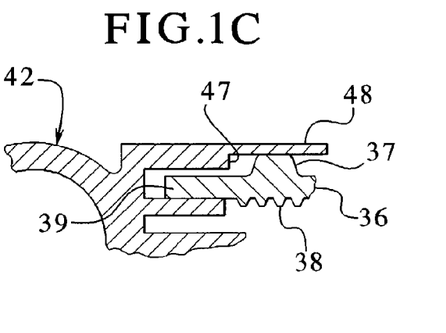
FIG. 1C is a schematic sectional view showing another embodiment of an interface between the shell and the tip protector.

Referring now to the figures, and in particular to FIGS. 1A to 1C, a connector of the present invention is illustrated. FIG. 1A illustrates that the connector 10 includes a cap 12. Generally, the components of the present invention, including the cap 12, are made of a plastic material such as polyethylene, polypropylene, nylon, polystyrene, polyester, PVC, a blend of various plastics or any other plastic or synthetic material that is capable of being washed and sterilized or substantially sterilized. As is illustrated below, certain components of the connector 10 seal to other components. These sealing components are generally made from compressible materials such as compressible rubber, e.g., silicone or the like.

The components of the connector 10 are constructed into desired shapes via any known method for producing plastic or rubber pieces, such as a molding process, e.g., an injection molding process. The compressible or rubber pieces may alternatively be cut and/or stamped from a larger piece of the compressible or rubber material. In alternative embodiments, one or more of the components, i.e., the plastic components, may alternatively be constructed from a metal, e.g., a noncorrosive metal such as stainless steel or aluminum, and may be formed via any known method of forming or stamping same.

The cap 12 includes a body 14 that is injection molded or blow molded to define a desired shape. Although FIG. 1A shows one embodiment of the connector and the cap 12, the body 14 of the cap 12 may be made in a variety of different shapes and sizes to mate with and/or work with various systems for introducing medical fluids into a patient. The various systems can be provided by other manufacturers or by the assignee of this invention. In one embodiment, the body 14 defines the following components or features.

The body 14 defines at least one receptacle 16. The receptacle 16 is a well or other liquid containing shape that encompasses a void except for a sealable side. The body 14 can define a variety of different receptacles 16; however, FIG. 1A shows an embodiment wherein the body 14 defines a single receptacle 16. A seal 18 encloses or caps off the receptacle 16. The seal 18 in an embodiment is a crosslinked elastomeric seal made from silicone. The seal may alternatively be made from any other type of rubber or compressible material such as neoprene, vinyl, viton, buna-n, butyl, EPDM, latex or the like.

The seal 18 can be made from solid or sponge rubber. In an embodiment, the seal 18 may be clear so that the user or patient can see a disinfectant 20 housed between the seal and the receptacle 16. In an embodiment, the seal 18 is coated with or impregnated with a disinfectant, which acts to further sterilize the connector 10.

In an embodiment, the seal 18 compresses against the walls of the receptacle 16, so that the disinfectant 20 residing within the receptacle 16 in any suitable form and/or manner cannot initially escape, even if the cap 12 of the connector 10 is turned so that the seal 18 faces downward and even if the patient or user moves, manipulates, shakes or otherwise causes the disinfectant 20 to move within the receptacle 16.

In an embodiment, the seal 18, compressed within the walls of the receptacle 16, is translatable so that the seal 18 can move towards an end of the receptacle 16. The method for translating the seal 18 is set forth in detail below in connection with FIGS. 3 to 7. In an alternative embodiment, the seal 18 is thin or otherwise frangible, e.g., is constructed from a thin plastic or metal-coated plastic sheet. The sheet is designed to rip when the patient or user applies pressure to the sheet, wherein the disinfectant flows through the ruptured sheet of the seal 18. In the alternative embodiment, the seal 18 would not compress against the walls of the receptacle 16; rather, a suitable adhesive would be used to secure the seal 18 to the receptacle 16, or the seal 18 could be adhered to the receptacle 16 via a known heat-shrinking or heating process.

The disinfectant 20 is adaptable to be any suitable type, form and/or amount of disinfectant that can sterilize or substantially sterilize plastic, rubber, metal or other like materials. In an embodiment, the disinfectant 20 is composed of povidone iodine. It should be appreciated that the povidone iodine can be provided in any suitable form and/or amount thereof. In an embodiment, a povidone iodine gel may have been subjected to gamma irradiation, steam sterilization and/or ethylene oxide.

In another embodiment, the disinfectant is or includes iodine-containing antimicrobials. In a further embodiment, the disinfectant uses or includes a povidone iodine (not in gel form) that is or may be subjected to gamma irradiation and/or steam sterilization. In still another embodiment, the disinfectant is or includes betadine. It should be appreciated that the disinfectant 20 of the present invention can alternatively be any desired disinfectant known to those of skill in the art.

The body 14 of the cap 12 also in an embodiment defines internal threads 22 and external threads 24. In the illustrated embodiment, the internal threads 22 and external threads 24 reside on the same end of the cap 12. The purpose of the inner and outer threads will be shown below. It is important to note, however, that the relative relationship between the internal threads 22 and the external threads 24 is not important to the operation of the present invention. In general, the body 14 of the cap 12 enables the first member to move along the central axis of the body 14 via one of the set of threads. The body 14 of the cap 12 also enables a second member to move along the central axis of the body 14. It is not important which member moves by engaging the internal threads 22 and which member moves in the other direction by engaging the external threads 24. An important aspect of the present invention, rather, is that two separate members may move inward and outward relative to the body 14 of the cap 12.

The inner threads 22 and the outer threads 24 may have any thread pitch desired by the implementor of the present invention. In the illustrated embodiment, the external threads 24 are slightly tapered, for example, at about one degree. In an alternative embodiment, the threads are straight, such as in a lead screw or ball screw. In the illustrated embodiment, the external threads 24 enable one member to translate relative to another, wherein the member eventually bottoms out or has a limited range of travel with respect to the external threads 24. Likewise, the inner threads 22 may be straight threads that allow a member to rotate freely in and out of the body 14 or the inner threads 22 may be tapered such that the member bottoms out as it inserts into the body 14.

The body 14 defines a passage 26 that enables a medical fluid such as a dialysate to move from one end of the cap 12 to another. The passage 26 can alternatively be the opening defined by the inner threads 22 and does not have to include the reduced tubing piece illustrated as the passage 26 in FIG. 1A. The passage 26, however, is sized to have approximately the same inner diameter as the tubes or catheters carrying the dialysate back and forth from a dialysate container and the peritoneal cavity of the patient.

In the illustrated embodiment, the body 14 defines a housing 28 at an end opposing the internal and external threads 22, 24. The housing 28 is sized to hold a septum 30. The housing 28 is swaged to the septum 30 or otherwise holds the septum 30 in a snug manner. The septum 30 cannot move in either axial direction relative to the body 14. The body 14 defines an end wall 32 having a smaller inner diameter than that of the housing 28, which also holds the compressible septum 30 in place. A suitable adhesive may also be employed to hold the septum 30 within the housing 28.

In an embodiment, the septum 30 is cylindrical as is the body 14 and the connector 10 in general. However, the septum 30, the body 14, and the connector 10 can each have alternative shapes such as being square or rectangular.

The septum 30 in an embodiment is made of a compressible or rubber material. The septum can be made from any type of rubber, including any of the above listed rubbers. As is well known in the art, the septum 30 defines a slit (not illustrated) which enables a tube or other type of fluid communication member to pass through a back wall 34 of the septum 30. The septum 30 in the illustrated embodiment generally defines a cap- or nut-shaped rubber or otherwise compressible piece having the back wall 34 and a cylindrical side wall 35 that extends from the back wall 34. The nut-shaped or cap-shaped septum in an embodiment is made as one piece, wherein the slit is made in the back wall 34. A tube or fluid communication member then inserts and resides inside a hollow chamber defined by the septum 30 and at some point is able to pass through the back wall 34.

In the illustrated embodiment, the connector 10 is configured so that the external threads 24 of the body 14 mate with internal threads of a shell 36. The shell 36 is a plastic or metal piece and may be of the same material as the body 14 of the cap 12. The shell 36 defines the internal threads 38 that mate with the external threads 24 of the body 14. The shell 36 can thus translate in either axial direction relative to the body 14 by rotating in a clockwise or counterclockwise direction about the body 14.

The shell 36 defines a tube or port 40, which in an embodiment is integrally formed with the shell 36, e.g., through an injection molding or blow molding process. The tube 40 extends inwardly into a cavity defined by the shell 36 and into the body 14 of the cap 12 through an opening defined by the end wall 32 of the body 14. The tube 40 also inserts into the cavity defined by the septum 30. When the shell 36 rotates about the outer threads 24 of the body 14 to a packaging position, an end 41 of the tube 40 abuts or is directly adjacent to the back wall 34 of the septum 30. For example, there may be a gap of about 0.010 in. (0.25 mm.) between the end 41 of the tube 40 and the back wall 34 of the septum 30.

The tube or port 40 also extends outwardly from the shell 36. The tube or port 40 sealingly connects to a tube (not illustrated) that runs to a dialysate container or a container housing the medical fluid that transfers through the connector 10 of the present invention. In an embodiment, the tube connecting to the dialysate bag press fits or sealingly fits over the port 40 in such a way that the dialysate does not leak from the interface of the flexible tube running to the dialysate container and the port 40. The tube of the dialysate bag can also connect to the port 40 via a solvent bond.

It should be appreciated that the dialysate is generally transferred back and forth, to and from, the dialysate container under its own weight and generally does not require an external pump or pressure system to drive the flow. Therefore, the fluid is not under substantial pressure and the seal required for the port 40 is not difficult to achieve. In an alternative embodiment, a hose clamp or other type of releasably fastenable device may be used to bolster the seal made between the flexible tube running to the dialysate bag and the port 40. Such interface is made readily and without requiring the patient or user to have an excessive amount of strength or to perform overly intricate operations.

A tip protector 42 fits over the shell 36 and at the same time fits into the interior cavity defined by the internal threads 22 of the body 14. The tip protector 42 is made in an embodiment of any of the plastic materials described above. The tip protector 42 defines a ring or handle 44 that enables the user or patient to remove the tip protector 42 from the shell 36 to begin using the connector 10. That is, the connector 10 is initially packaged with the tip protector 42. The first time the user or patient uses the tip protector 42, the user or patient removes the tip protector and discards it.

The tip protector 42 serves a number of purposes in protecting the connector 10 prior to use. The tip protector 42 provides a microbial barrier. The tip protector 42 disallows bacteria and other harmful airborne agents from entering the body 14 of the cap 12 prior to use. Just before attaching the cap 12 to a mating connector (see mating connector 60 in FIGS. 2 through 7), the patient or operator removes the tip protector 42. In this way, the inside of the body 14 of the cap 12 is only exposed to open air for a very short amount of time.

In an embodiment, for example, when the connector 10 is to be used for CAPD, the tip protector 42 also sets the shell 36 at the appropriate distance relative to the body 14 for packaging the connector 10. That is, the tip protector 42 helps to set the end 41 of the tube 40 of the shell 36 directly adjacent to the back wall 34 of the septum 30.

Prior to use, the tube 40 does not insert into or open up the slit (not illustrated) in the back wall 34 of the septum 30. However, it is desirable not to have the end of the tube or port 40 too far away from the back wall 34 of the septum 30 upon packaging the connector 10 for a couple of reasons. First, it is desirable to package the connector 10 in as small a space as possible. If the connector 10 is packaged so that the end 41 resides away from the back wall 34, then the connector 10 is longer in an axial direction than it needs to be. Second, it is desirable not to make the user or patient rotate the shell 36 more than is necessary to insert the tube 40 through the slit of the back wall 34 of the septum 30 to begin using the connector 10.

FIGS. 1A and 1B illustrate that the tip protector 42 in an embodiment defines threads 46 that engage some of the internal threads 38 of the shell 36. The shell 36 only threads into the tip protector 42 so far before the shell 36 bottoms out against a cylinder 48 defined by the tip protector 42. FIG. 1B illustrates that in an embodiment, the outside of the shell 36 includes a taper 35 at the end of the portion of the shell 36 defining the threads 38. As the tip protector 42 threads into the shell 36, the taper 35 increasingly presses against the inside of the cylinder 48. In an embodiment, the cylinder 48 of the tip protector 42 defines a stepped portion 47 that facilitates the engagement between the taper 35 of the shell 36 and the tip protector 42.

Thus, when the connector 10 is packaged, the tip protector 42 can be placed against or abutted against the body 14 of the cap 12 before the shell 36 threads onto the body 14 and onto the threads 46 of the tip protector 42. The shell 36 threads over the external threads 24 of the body 14 and passes or translates past the body 14 a desired distance defined by the threads 46 of the tip protector 42. It is at this point that the end 41 of the tube 40 abuts or is directly adjacent to the end wall 34 of the septum 30.

It should be appreciated that the cylinder 48 of the tip protector 42 is not threaded and does not threadingly engage the shell 36 so that the cylinder 48 simply slides over and translates relative to the shell 36. It should also be appreciated that to remove the tip connector 42, the user holds the shell 36 and rotates the ring 44 a number of turns.

FIG. 1C illustrates an alternative embodiment that is used, for example, when the connector 10 performs APD. The tip protector 42 simply slides and possibly slightly press fits onto or into the body 14 of the cap 12. Here, the tip protector 42 does not define the threads 46. The shell 36 may or may not be tapered and may contain a stepped member 37, wherein the member 37 is intended to slightly frictionally engage the inner wall of the cylinder 48. The internal threads 38 of the shell 36 stop before reaching the inner portion 39 of the shell 36 that abuts the tip protector 42.

When the connector is initially packaged, the body 14 cannot move relative to the shell 36 until the tip connector 42 is removed. This is important to ensure that the seal 18 is not ruptured or displaced prior to using the connector 10. The tip protector 42 also includes an inner extension 50 that extends into the chamber created by the internal threads 22 of the body 14. The extension 50 extends so that it abuts or is directly adjacent to the seal 18. This ensures that prior to use, the seal 18 does not loosen and move away from the receptacle 16 to thereby create a leaky connector 10. Thus, it should be appreciated that the tip connector 42 enables the connector 10 to be handled and shipped without destroying the seal 18 and/or losing the disinfectant 20 maintained by the seal 18.

Figure 2:
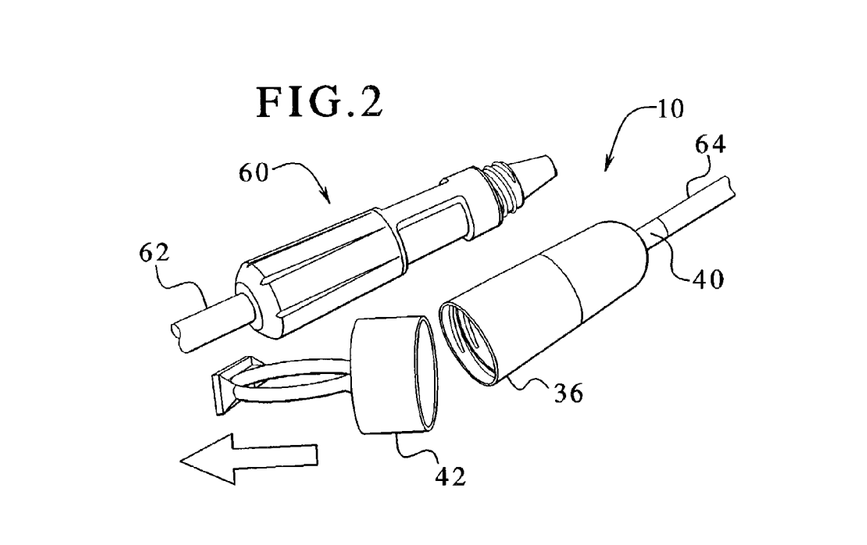
FIG. 2 is a perspective view illustrating a part of the process for connecting the connector and cap of the present invention to a transfer set, which connects a catheter to a patient.
Figure 3:
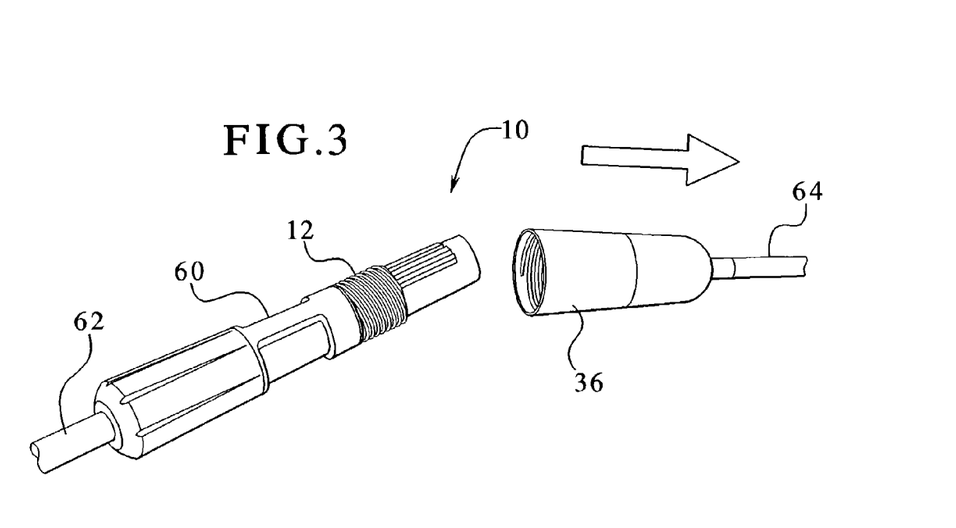
FIG. 3 is a perspective view illustrating another part of the process for connecting the connector and cap of the present invention to a transfer set, which connects a catheter to a patient.

Referring now to FIGS. 2 and 3, one embodiment for connecting the connector 10 of the present invention to a mating connector 60 is illustrated. The connector 10 may be adapted to operate with many different types of connectors or devices that provide a catheter 62 that inserts into the peritoneal cavity of the patient. In an embodiment, the connector 10 is adapted to attach to a transfer set that is illustrated in FIG. 2 as the connector 60. The transfer set in one embodiment is a MiniSet™ manufactured by the BAXTER INTERNATIONAL INC. Although the MiniSet™ 60 is one operable embodiment of the transfer set or catheter device, the connector 10 can operate with any type of device that couples to a tube or catheter, which inserts into the patient's peritoneal cavity.

In FIG. 2, the tip protector 42 is unsecured or removed from the shell 36 of the connector 10. The port 40 of the shell 36 of the connector 10 is illustrated as sealingly connecting to a flexible tube 64 that runs to the dialysate container or bag.

FIG. 3 illustrates that after inserting the connector 10 onto the connector or transfer set 60, the shell 36 connected to the tube 64 threads off of and away from the cap 12. The connector 10 threads onto the connector or transfer set 60 using the internal threads 22 defined by the body 14 of the cap 12, which are exposed when the tip protector 42 is removed.

FIG. 3 illustrates a point in the process when the patient has completed the transfer of the dialysate from the dialysate container into the peritoneal cavity, or FIG. 3 illustrates a point in the process when the patient or user has finished draining spent dialysate from the peritoneal cavity into the dialysate container. In either situation, when the shell 36 threads off of the container 10, the cap 12 of the container remains fixed to the connector or transfer set 60 and thereby caps off the transfer set 60. In this manner, because the sterility of cap 12 is maintained and cap 12 remains functional, a separate cap which would normally have to be taken off and re-placed onto the transfer set 60 before and after each use is no longer necessary.

Figure 4:
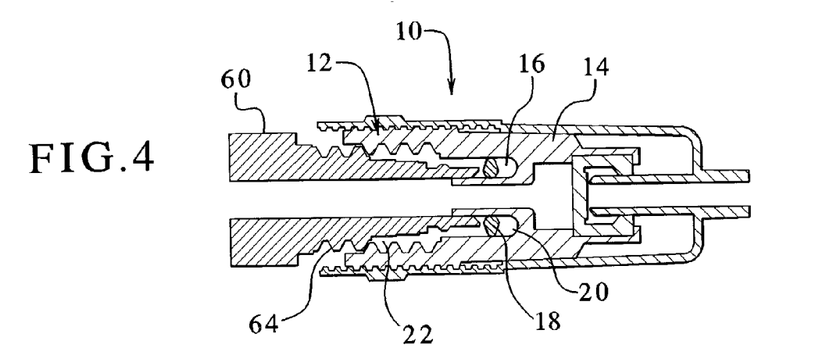
FIG. 4 is an elevation view illustrating one step for using the connector and cap of the present invention to insert and/or remove a medical fluid into/from a patient.

Referring now to FIGS. 4 to 7, one embodiment of a method for removing spent dialysate and inserting new dialysate into a patient in a substantially sterilized environment is illustrated. FIG. 4 illustrates a point in the process when the tip protector 42 has been removed and the transfer set or connector 60 is ready to be connected to the connector 10. At this point, the connector or transfer set 60 has not engaged the seal 18 to thereby rupture or displace the seal, which displaces the disinfectant 20. The connector or transfer set 60 includes external threads 64 that mates with the internally facing threads 22 of the body 14 of the cap 12.

Figure 5:
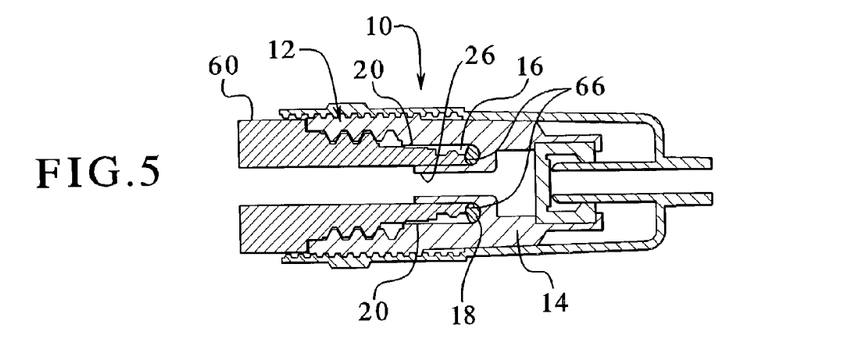
FIG. 5 is an elevation view illustrating another step for using the connector and cap of the present invention to insert and/or remove a medical fluid into/from a patient.

When the user or patient desires to connect the catheter from the peritoneal cavity to the connector 10, the user or patient threads the connector or transfer set 60 (connecting to the catheter extending to the peritoneal cavity) into the body 14 of the cap 12 so that ends 66 of the connector transfer set 60 engage the seal 18 and either move it or rupture it (best seen in FIG. 5). That is, the ends 66 apply a translational force to the seal 18 which causes the seal 18 to compress against the disinfectant 20. Eventually, as the user screws the connector 60 into the body 14, the pressure becomes too much for the seal to handle, whereby the seal either moves so that the disinfectant leaves the receptacle 16 and squirts out around the seal 18 and the ends 66 pierce, or the seal ruptures (thin sheet seal embodiment described above) and the disinfectant 20 runs out over the external threads 64 of connector 60.

In the illustrated embodiment, the seal 18 remains intact but moves or displaces the disinfectant 20 to run out over the outside of the threads 64 of the connector 60, so that microorganisms contained thereon are substantially destroyed. The seal 18 as illustrated may be made in a teardrop-type shape wherein the blunt end of the teardrop has more sealing force than the tapered or sharper end of the seal 18. In this manner, the sharper or tapered end may slightly deform as the blunt end is dragged along the surface of the receptacle 16.

The mating connector 60 in an embodiment is sized to engage and slide along the passage 26 of the body 14. This also aids in dispersing the disinfectant 20 onto the outside of the mating connector 60 to disinfect the engaging threads. That is, the disinfectant will take the path of least resistance and tend to move into the open cavity defined between the outside of the connector 60 and an inner wall of the body 14, rather than squeezing through the friction fit between the inner opening of the connector 60 and the passage 26.

Figure 6:
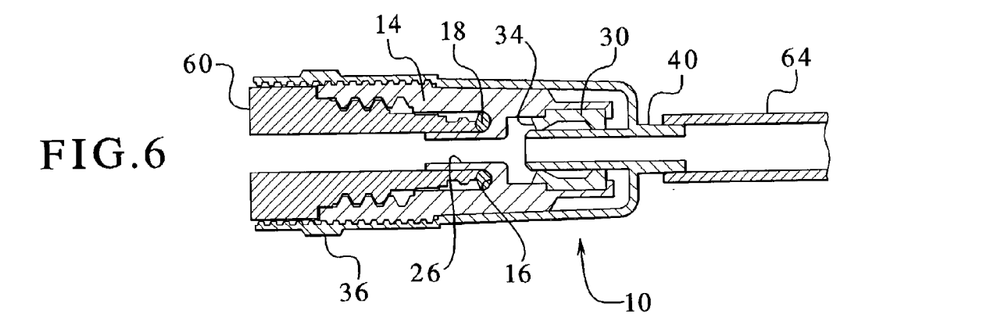
FIG. 6 is an elevation view illustrating a further step for using the connector and cap of the present invention to insert and/or remove a medical fluid into/from a patient.

Referring now to FIG. 6, after the mating connector or transfer set 60 bottoms out against the body 14, i.e., pushes the seal 18 all the way against the receptacle 16 of body 14. The assembly of the connector 10 to the mating connector 60 is now complete, so that the sealed end of the body 14 made by the slit septum 30 can be unsealed or opened. To break the seal of the septum 30, the user or patient rotates the shell or shell 36 relative to the body 14 wherein the threads of the shell 36 turn against the threads of the body 14. The shell 36 thereby translates towards the mating connector 60, so that the tube or port 40 of the shell 36 pierces through the back wall 34 of the septum 30 and through the slit defined by the back wall 34. At this point, fluid communication exists between the peritoneal cavity of the patient and the dialysate bag.

Thus, at the point illustrated in FIG. 6, the dialysate fluid may flow in either direction. That is, if the patient is removing spent dialysate from the peritoneal cavity, the dialysate fluid can flow from the catheter in the cavity into the mating connector 60, through the passage 26 of the body 14, out the port 40 and into the flexible tube 64 running to the dialysate container or bag.

In CAPD, to remove the spent dialysate from the peritoneal cavity, the user or patient typically opens a clamp on the upstream side of the mating connector 60 or integrally formed with the mating connector 60, wherein the spent dialysate runs into an awaiting container. The flex tube 64 typically runs to a "Y" connection, wherein one leg extends to the spent dialysate container and another leg extends to a new dialysate bag. When the old dialysate has been drained into the spent bag, the operator opens a fill-bag clamp that enables the new dialysate to run from the flexible tube 64, to the port 40, through the septum 30, through the passage 26, into the internal diameter of the mating connector 60 and into the catheter leading into the peritoneal cavity. With APD, one or more pumps automatically pull the spent dialysate from the patient's peritoneal cavity and places fresh dialysate into same.

FIGS. 4, 5 and 6 illustrate one complete cycle of flushing old or spent dialysate and replenishing new dialysate into the peritoneal cavity. With both CAPD and APD, the cycle is repeated a number of times. Obviously, many other different types of medical fluids may be substituted for the dialysate described herein, wherein a number of medical procedures may be performed using the connector 10 having the cap 12 of the present invention.

Figure 7:
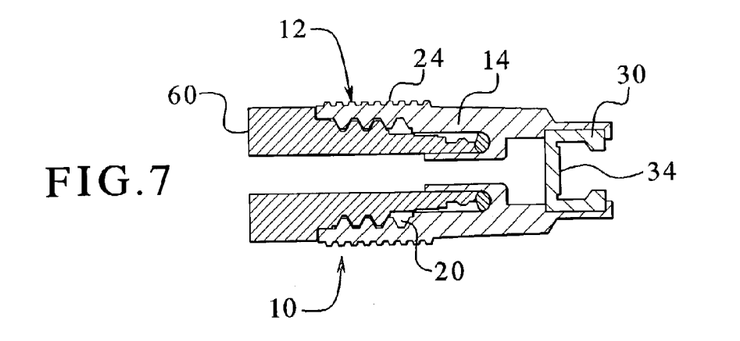
FIG. 7 is an elevation view illustrating still another step for using the connector and cap of the present invention to insert and/or remove a medical fluid into/from a patient.

Referring now to FIG. 7, when the transfer of fluids has been exchanged, the user or patient removes the shell 36 from the cap 12, so that the tube 40 of the shell 36 removes from the septum 30. When removed, the slit in the wall 34 of the septum 30 closes and the end of the body 14 is once again sealed. The body 14 remains in the threaded position with respect to the mating connector 60, so that the disinfectant 20 is maintained between the mating threads and the open area between the mating connector 60 and the body 14.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A connector for making a resealable fluid path comprising:
   a cap defining including threads and a fluid flow passage, the fluid flow passage including a sealed end;
   an amount of a disinfectant sealed within the cap; and
   a shell including threads configured to mate with the threads of the cap, the shell including a fluid communication member;
   wherein the fluid communication member is configured to pierce the sealed end of the cap to establish fluid communication with the fluid flow passage when the shell is moved with respect to the cap.

2. The connector of claim 1, wherein the disinfectant comprises povidone iodine.

3. The connector of claim 1, which includes a tip protector that abuts an end of the shell that opposes the sealed end of the cap.

4. The connector of claim 1, wherein the shell attaches to a fluid line running to a dialysate container and the cap attaches to a fluid line running to a patient.

5. The connector of claim 1, wherein the sealed end of the cap includes a slit septum.

6. The connector of claim 1, which includes an elastomeric seal that seals the amount of disinfectant about the fluid flow passage.

* * * * *

UNITED STATES PATENT AND TRADEMARK OFFICE
CERTIFICATE OF CORRECTION

| | | |
|---|---|---|
| PATENT NO. | : 7,198,611 B2 | Page 1 of 1 |
| APPLICATION NO. | : 10/074532 | |
| DATED | : April 3, 2007 | |
| INVENTOR(S) | : Connell et al. | |

It is certified that error appears in the above-identified patent and that said Letters Patent is hereby corrected as shown below:

IN THE CLAIMS:

In Claim 1, column 12, line 40, please change "a cap defining including" to --a cap including--.

Signed and Sealed this

Thirteenth Day of July, 2010

David J. Kappos
*Director of the United States Patent and Trademark Office*